United States Patent [19]

Murakata et al.

[11] Patent Number: 4,877,776
[45] Date of Patent: Oct. 31, 1989

[54] K-252 COMPOUNDS

[75] Inventors: Chikara Murakata, Asaka; Akira Sato, Machida; Masaji Kasai, Fujisawa; Eiji Kobayashi, Shizuoka; Makoto Morimoto, Shizuoka; Shiro Akinaga, Shizuoka, all of Japan

[73] Assignee: Kyowa Hakko Kogyo Co., Ltd., Tokyo, Japan

[21] Appl. No.: 288,787

[22] Filed: Dec. 22, 1988

[30] Foreign Application Priority Data

Dec. 24, 1987 [JP] Japan .................. 62-327857

[51] Int. Cl.⁴ .................. A61K 31/71; C12P 19/38; C07H 19/04
[52] U.S. Cl. .................. 514/43; 540/472; 424/122; 435/164; 536/24
[58] Field of Search .................. 424/122; 435/169; 514/43; 536/24; 540/472

[56] References Cited

U.S. PATENT DOCUMENTS 4,555,402  9/1984  Matsuda et al. .................. 424/122

FOREIGN PATENT DOCUMENTS 61-176531  8/1961  Japan .
60-185719  9/1985  Japan .
62-120388  6/1987  Japan .
62-155284  7/1987  Japan .
62-155285  7/1987  Japan .
62-164626  7/1987  Japan .
62-240689  10/1987  Japan .

OTHER PUBLICATIONS

J. Antibiotics, 30(4), 275–282 (1977), Omura et al., "A New Alkaloid AM–2282 of Streptomyces Origin . . . ".
J.C.S. Chem Comm, 800–801 (1978) Furasaki, et al., "X–Ray Crystal Structure of Staurosporine . . . ".
J. Antibiotics 38(10), 1437–1439, (1985), Sezaki, et al., "A New Antibiotic SF–2370 . . . ".

Primary Examiner—Anton H. Sutto
Assistant Examiner—Miriam Sohn
Attorney, Agent, or Firm—Michael N. Meller

[57] ABSTRACT

A K-252 compound represented by the formula:

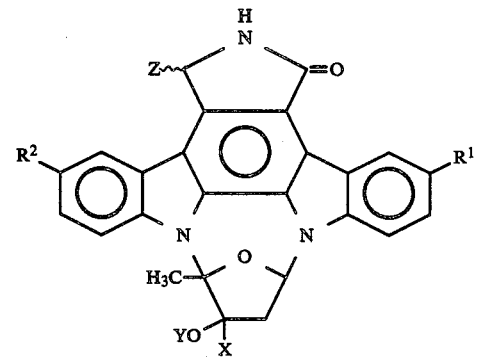

wherein $R^1$ and $R^2$ are independently H or OH; X represents COOH, COOR or $CH_2OH$; Y represents H, R or COR; and Z represents OH, OR or SR, wherein R represents lower alkyl has C-kinase inhibitory activity and is expected to be useful as an active ingredient of anti-tumor agents, etc.

15 Claims, No Drawings

K-252 COMPOUNDS

BACKGROUND OF THE INVENTION

The present invention relates to novel compounds which inhibit protein kinase C (hereafter referred to as C-kinase) and have activities such as anti-tumor activity.

C-kinase is a protein kinase which is activated depending upon phospholipids and calcium and widely distributed over tissues and organs in the living body. In recent years, it has become known that this enzyme plays an extremely important role in cell membrane receptor transduction mechanism in which many hormones, neurotransmitters, etc. are concerned. As examples of physiological response induced by the signal transduction system in which C-kinase participates, there have been reported serotonine release from platelets, lysosomal enzyme release and aggregation, superoxide formation and lysosomal enzyme release from neutrophil leukocytes, epinephrine release from adrenal medulla, secretion of aldosterone from renal glomerulus, secretion of insulin from Langerhans' islet, histamine release from mast cells, acetylcholine release from ileum, contraction of vascular smooth muscle, and the like. C-kinase is also supposed to be concerned in cell growth and carcinogenetic mechanism [Y. Nishizuka, Science, 225, 1365 (1984); H. Rasmussen et al., Advance in Cyclic Nucleotide and Protein Phosphorylation Research, vol. 18, p. 159, edited by P. Greengard and G. A. Robinson, Raven Press, New York, 1984]. It has thus been clarified that C-kinase takes part in many important physiological responses in vivo and various morbid conditions. Therefore, it is expected that a wide variety of diseases such as diseases of the circular system, inflammatory diseases, allergy and tumor can be prevented or treated by artificially inhibiting C-kinase activity by the use of specific inhibitors, etc.

On the other hand, it has been found that antipsychotic drugs such as trifluoperazine and chlorpromazine, dibenamine and tetracaine which are known as local anesthetics, calmodulin inhibitor W-7 [N-(6-aminohexyl)-5-chloro-1-naphthalenesulfonamide], etc. possess C-kinase inhibitory activity. However, the C-kinase inhibitory activity is not the main activity of these drugs, and they only exhibit low inhibitory activity against C-kinase with low specificity [Y. Nishizuka et al., J. Biol. Chem., 255, 8378 (1980); R. C. Schatzman et al., Biochem. Biophys. Res. Commun., 98, 669 (1981); B. C. Wise et al., J. Biol. Chem., 257, 8489 (1982)].

Further, K-252 and KT-5556 represented by the following formula (II) and K-252 derivatives in which $R_A$ and $R_B$ are modified are known (with K-252, see Japanese Published Unexamined Patent Application No. 41489/85 and U.S. Pat. No. 4,555,402; with KT-5556, see Japanese Published Unexamined Patent Application No. 176531/86; and with the K-252 derivatives, see Japanese Published Unexamined Patent Application Nos. 155284/87 and 155285/87).

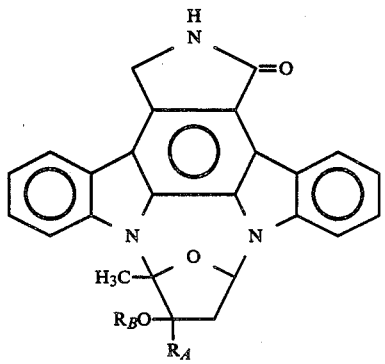

K-252 (IIa): $R_A = CO_2CH_3$, $R_B = H$

KT-5556 (IIb): $R_A = CO_2H$, $R_B = H$

In Japanese Published Unexamined Patent Application No. 41489/85, it is described that K-252 has activity to inhibit histamine release and anti-allergic activity, and in Japanese Published Unexamined Patent Application Nos. 155284/87 and 155285/87, it is described that the K-252 derivatives have C-kinase inhibitory activity and antivity to inhibit histamine release. It is described in Japanese Published Unexamined Patent Application No. 176531/86 that KT-5556 has activity to inhibit histamine release. In addition, compounds that are assumed to be identical with K-252 or KT-5556 have been reported as antibacterial substances [M. Senzaki et al., J. Antibiotics, 38, 1437 (1985)]. In this publication, a compound of the above formula wherein $R_A=CO_2CH_3$ and $R_B=COCH_3$ is also disclosed. The compound assumed to be identical with K-252 and its halogen derivatives are disclosed in Japanese Published Unexamined Patent Application Nos. 120388/87 and 164626/87 and derivatives wherein $R_A$ is modified are disclosed in Japanese Published Unexamined Patent Application No. 240689/87, all as the compounds possessing hypotensive action and diuretic action.

Furthermore, Staurosporine having the following structure and antibacterial activity is known as a compound having a structure relatively akin to that of K-252 [S. Omura et al., J. Antibiotics, 30, 275 (1977); A. Furusaki et al., J. Chem. Soc. Chem. Commun., 800 (1978); Japanese Published Unexamined Patent Application No. 185719/85].

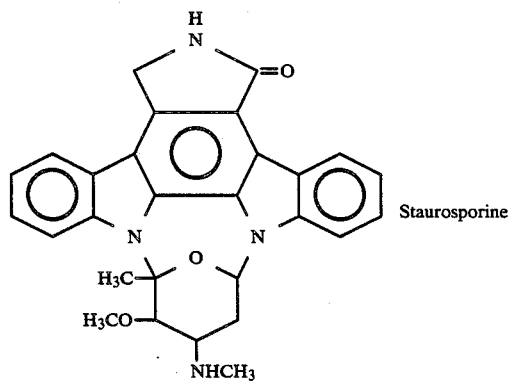

Staurosporine

A novel active ingredient for an anti-tumor agent, etc. which has a high C-kinase inhibitory activity is always in demand.

SUMMARY OF THE INVENTION

According to the present invention, there are provided novel derivatives of K-252 represented by formula (I):

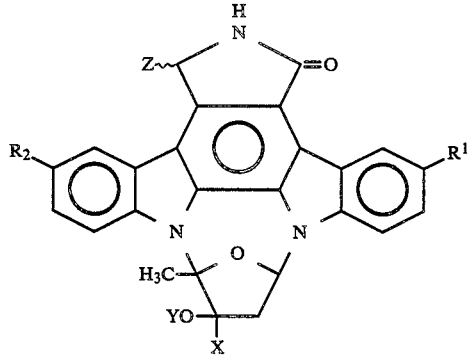

wherein $R^1$ and $R^2$ are independently H or OH; X represents COOH, COOR or $CH_2OH$; Y represents H, R or COR; and Z represents OH, OR or SR, wherein R represents lower alkyl.

Compound (I) has C-kinase inhibitory activity and is expected to be useful as an active ingredient of antitumor agents, etc.

DETAILED DESCRIPTION OF THE INVENTION

The compounds represented by formula (I) are hereinafter referred to as Compound (I). Compounds represented by formulae with other numbers are referred to similarly. Compound (I) possesses an excellent C-kinase inhibitory activity and also possesses cell growth inhibitory activity.

In the definitions of formula (I), the lower alkyl includes a straight chain or branched alkyl having 1 to 4 carbon atoms, for example, methyl, ethyl, n-propyl, i-propyl, n-butyl and t-butyl.

The compounds of the present invention can be obtained as diastereoisomers at the carbon to which the group Z is bound using, as a starting compound, K-252, etc. which are optically active. All possible stereoisomers and mixtures thereof are also included in the present invention.

Processes for producing Compound (I) are described below. However, production of Compound (I) is not deemed to be limited to these processes.

Compound (I) can be produced from K-252, etc. represented by formula (II) by various synthetic means.

In the processes shown below, in cases where the defined groups change under the conditions shown or are inadequate for the practice of the processes, the processes can be easily operated by applying thereto means conventionally used in organic synthetic chemistry, for example, protection of functional groups and removal of the protective groups [e.g., Green: Protective Groups in Organic Synthesis, John Wiley & Sons Incorporated (1981)].

PROCESS 1

Synthesis of Compound (I-1) wherein Z is introduced into the lactam ring of Compound (III)

1-1: Compound wherein Z is OR (I-1-1)

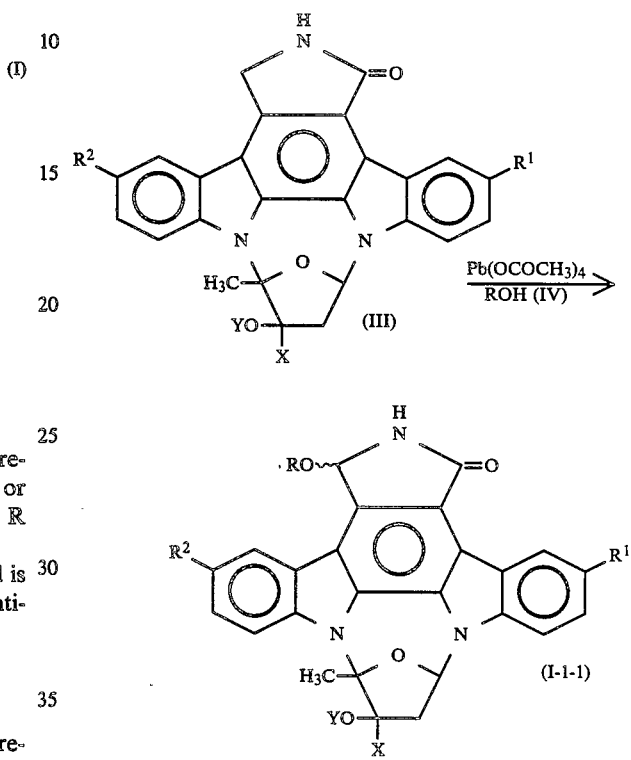

In the formulae, $R^1$, $R^2$, X, Y and R have the same significances as defined above.

Compound (I-1-1) can be obtained by subjecting Compound (III) [including Compound (II)] to reaction with lead tetraacetate in acetic acid and then treating the compound with a large excess of an alcohol (IV). Lead tetraacetate is used in an amount of 1 to 1.1 equivalents based on Compound (III). The reaction is usually carried out at room temperature and completed in 7 to 10 hours.

1-2: Compound wherein Z is OH (I-1-2)

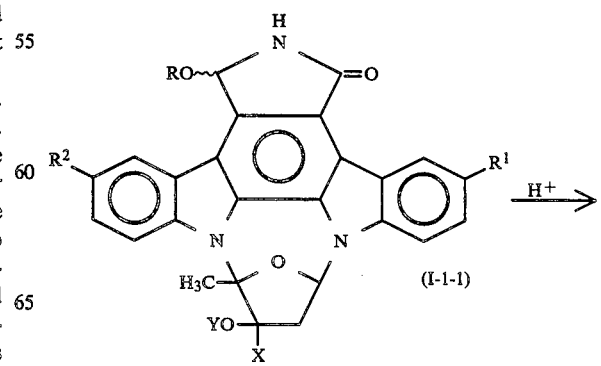

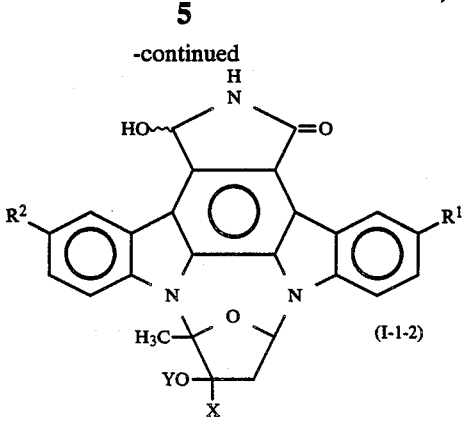

In the formulae, $R^1$, $R^2$, X, Y and R have the same significances as defined above.

Compound (I-1-2) can be obtained by subjecting Compound (I-1-1) obtained in Process 1 to reaction in hydrated dioxane in the presence of a suitable acid catalyst, for example, camphorsulfonic acid. The acid is used in an amount of 0.04 to 0.05 equivalent based on Compound (I-1-1). Hydrated dioxane contains 20 to 50% water. The reaction is usually carried out at 80° to 100° C. and completed in 4 to 5 hours.

1-3: Compound wherein Z is SR (I-1-3)

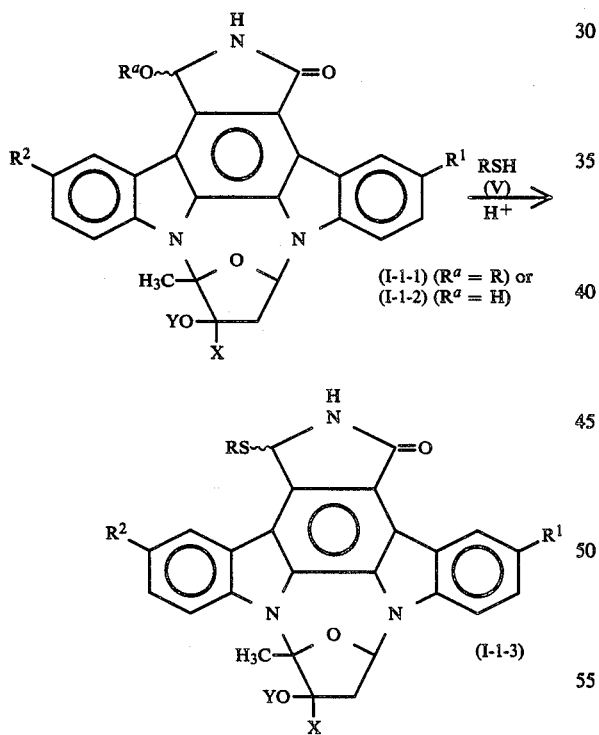

In the formulae, $R^1$, $R^2$, X, Y and R have the same significances as defined above and $R^a$ represents H or R.

Compound (I-1-3) can be obtained by subjecting Compound (I-1-1) or (I-1-2) to reaction with a thiol (V) in an appropriate inert solvent, for example, tetrahydrofuran (THF) in the presence of a suitable acid catalyst, for example, camphorsulfonic acid. Compound (V) and the acid catalyst are used in large excess and in an amount of 0.02 to 0.05 equivalent, respectively, based on Compound (I-1-1) or (I-1-2). The reaction is usually carried out at room temperature and completed in 0.5 to one hour.

In Process 1 above, in cases where the group X or OY or the like is a functional group inadequate for the reaction, the aforesaid steps such as protection of the functional group and removal of the protective group can be suitably added (for example, see Examples 3, 8, etc.).

Compound (I-1) obtained by Process 1 can be used as the intermediates for further synthesizing novel K-252 derivatives by Processes 2, 3, etc. described below.

PROCESS 2

Synthesis of Compound (I-2) wherein X is modified 2-1: Compound (I-2-1) wherein X is COOR

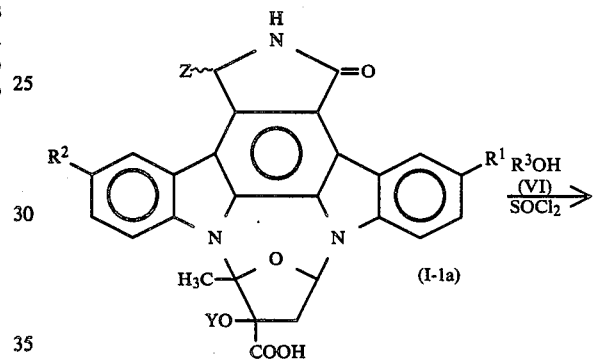

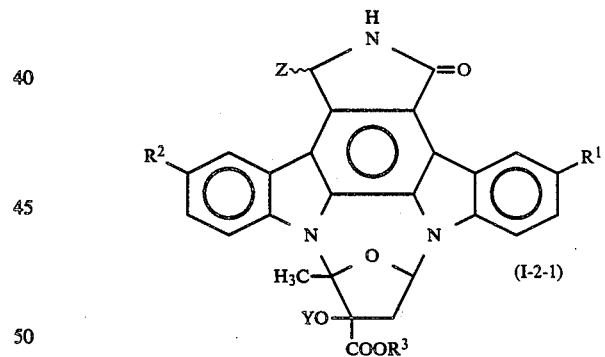

In the formulae, $R^3$ represents R, and $R^1$, $R^2$, R, Y and Z have the same significances as defined above.

Compound (I-2-1) can be obtained by adding an alcohol (VI) and an excess amount of thionyl chloride to Compound (I-1a) [Compound (I-1) wherein X is COOH] and heating the mixture under reflux. Thionyl chloride is usually used in an amount of about one tenth (volume ratio) of the amount of Compound (VI) used also as a solvent. The reaction is carried out in the range of 60° C. to the boiling point of Compound (VI) and almost completed in an hour to one day.

2-2: Compound (I-2-2) wherein X is CH$_2$OH

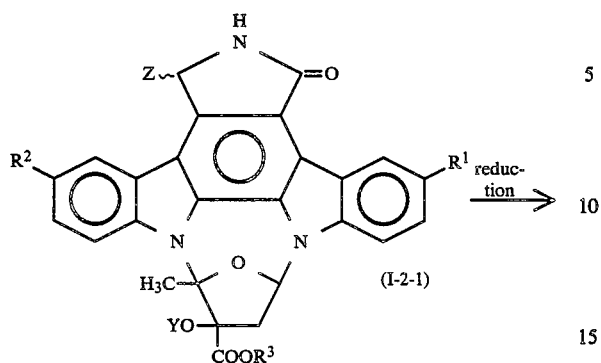

(I-2-1)

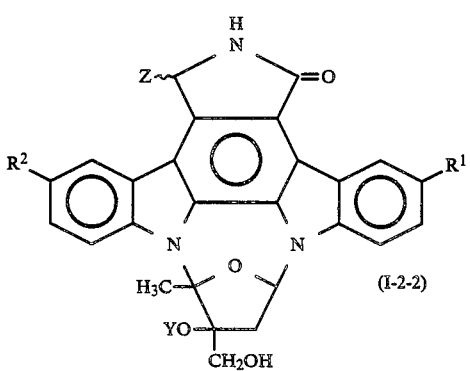

(I-2-2)

In the formulae, $R^1$, $R^2$, $R^3$, Y and Z have the same significances as defined above.

Compound (I-2-2) can be obtained by subjecting the ester (I-2-1) obtained by Process 2-1 to reaction with a suitable reducing agent, for example, sodium borohydride in an appropriate inert solvent, for example, hydrated THF. The reducing agent is used in an amount to 3 to 5 equivalents based on Compound (I-2-1). The reaction is usually carried out at 0° to 20° C. and completed in 1 to 12 hours.

PROCESS 3

Synthesis of Compound (I-3) wherein Y is modified 3-1: Compound (I-3-1) wherein Y is R

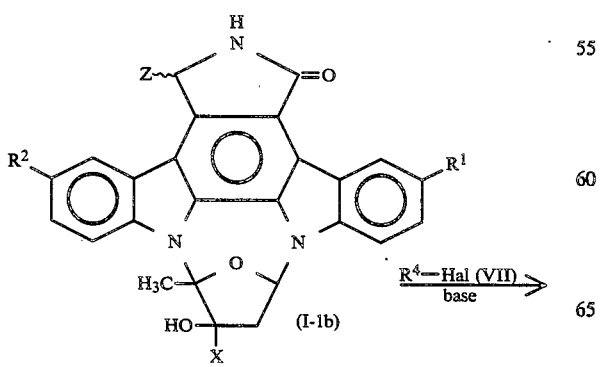

(I-1b)

-continued

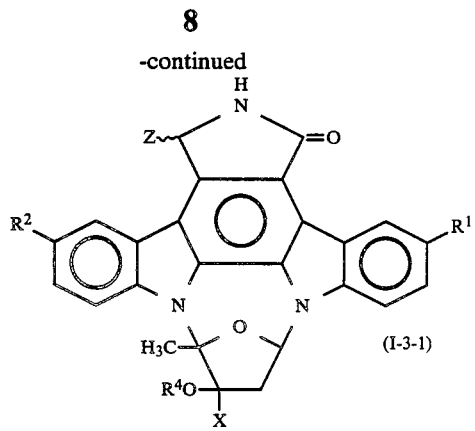

(I-3-1)

In the formulae, $R^4$ represents R; Hal represents a halogen; and $R^1$, $R^2$, R, X and Z have the same significances as defined above.

Compound (I-3-1) can be obtained by subjecting Compound (I-1b) [Compound (I-1) wherein Y is H] to reaction with a lower alkyl halide (VII) in a solvent inert to the reaction in the presence of a base. As Compound (VII), iodides and bromides which are highly reactive are preferred. The base includes sodium hydride, potassium t-butoxide, etc. Compound (VII) and the base are usually used in an equivalent amount based on Compound (I-1b). The inert solvent includes dimethylformamide (DMF), THF, etc. The reaction is usually carried out at 0° C. to room temperature and completed in 20 minutes to one hour.

3-2: Compound (I-3-2) wherein Y is COR

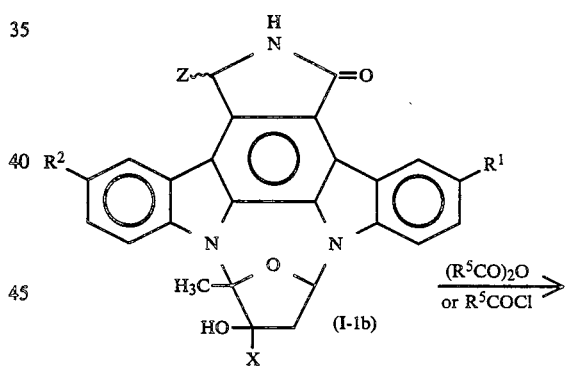

(I-1b)

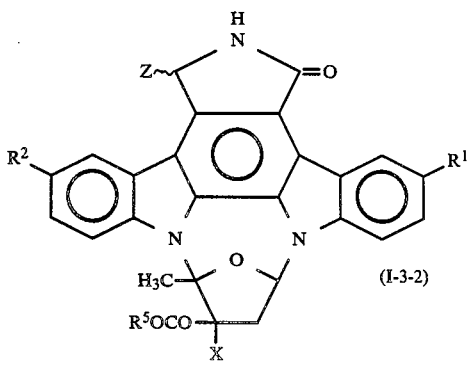

(I-3-2)

In the formulae, $R^5$ represents R, and $R^1$, $R^2$, R, X and Z have the same significances as defined above.

Compound (I-3-2) can be obtained by subjecting Compound (I-1b) to reaction with an acylating agent [$(R^5CO)_2O$, $R^5COCl$, or the like] in the presence of a base. The base includes pyridine, triethylamine, etc. The acylating agent is used in an amount of 1 to 2 equivalents based on Compound (I-1b). The reaction is usually carried out in pyridine as the solvent at 0° to 30° C. and completed in 1 to 12 hours.

By operating the above-described Processes 1 to 3 in a suitable combination, Compound (I) having a desired functional group at a desired position can be obtained.

Compound (I) can also be obtained by applying Process 2 or 3 to the lactam (III) [including Compound (II)] and then applying Process 1.

In each of the foregoing processes, isolation and purification of the product after completion of the reaction can be carried out by methods used in conventional organic synthesis, for example, by an appropriate combination of extraction, crystallization, chromatography, etc.

Compound (I) shows a marked cell growth inhibitory activity against human uterine cervical cancer HeLa cells, human breast cancer cell MCF7, human colon adenocarcinoma cell COLO320DM, human lung differented squamous cell carcinoma cell PC-10, etc. and accordingly, anti-tumor compositions comprising compound (I) as an effective ingredient are provided.

When Compound (I) is used as an anti-tumor composition, each compound is dissolved in physiological saline or a solution of glucose, lactose or mannitol for injection, and usually intravenously administered as an injection in a dose of 0.01 to 20 mg/kg. Alternatively, the compound may be freeze-dried in accordance with the Japanese Pharmacopoeia or may be prepared into injectable powder by adding sodium chloride thereto. Further, the anti-tumor composition may also contain pharmacologically acceptable well-known diluents, adjuvants and/or carriers such as salts which satisfy requirements for medical use. In cases where the compound is used as an injection, it is sometimes preferred to use auxiliary agents which enhance the solubility. Doses may be appropriately varied depending upon the age and conditions. Administration schedule can also be varied depending upon the conditions and dose. For example, the compound is administered once a day (by single administration or consecutive administration) or intermittently by one to three times a week or once every three weeks. Further, oral administration and rectal administration are also possible in the same dose and in the same manner. The compound can be administered, with appropriate adjuvants, as tablets, powders, granules, syrup, etc. for oral administration and as suppositories for rectal administration.

Representative examples of Compound (I) obtained by the processes described above are shown in Table 1 and the intermediates thereof are shown in Table 2. Examples of preparation of the Compound (I), examples of preparation of the intermediates thereof and pharmacological activities of representative Compound (I) are shown in Examples, Reference Examples and Experimental Examples, respectively.

TABLE 1

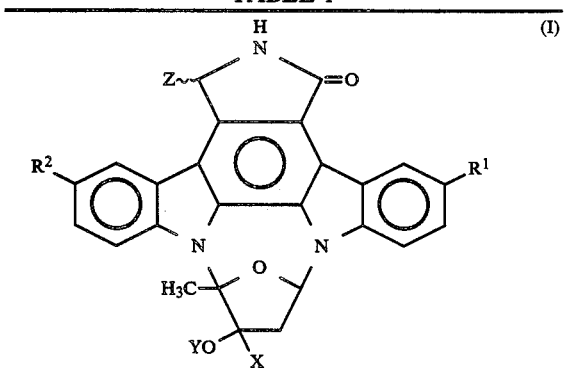

| Compound No. | Example No. | $R^1$ | $R^2$ | X | Y | Z |
|---|---|---|---|---|---|---|
| 1 | 1 | H | H | $CO_2CH_3$ | $CH_3$ | $OCH_3$ |
| 2 | 2 | H | H | $CO_2CH_3$ | $COCH_3$ | $OC_2H_5$ |
| 3 | 3 | H | H | $CO_2CH_3$ | H | $OC_2H_5$ |
| 4 | 4 | H | H | $CO_2CH_3$ | H | $SC_2H_5$ |
| 5 | 5 | H | H | $CO_2CH_3$ | H | OH |
| 6 | 6 | H | H | $CH_2OH$ | H | OH |
| 7 | 7 | H | H | $CH_2OH$ | H | $SC_2H_5$ |
| 8 | 8 | OH | H | $CO_2CH_3$ | H | OH |

TABLE 2

Intermediates

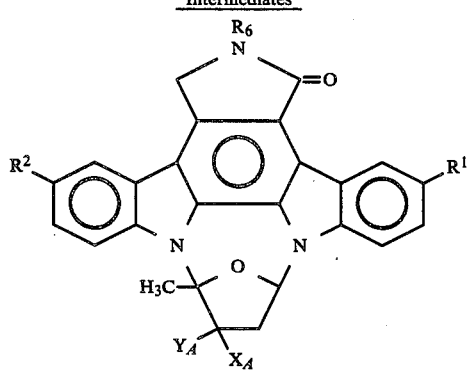

| Compound No. | Reference Example No. | $R^1$ | $R^2$ | $R^6$ | $X_A$ | $Y_A$ |
|---|---|---|---|---|---|---|
| a | 1 | H | H | H | $CO_2CH_3$ | $OCH_3$ |
| b |  | H | H | H | $CO_2CH_3$ | $OCOCH_3$ |
| c | 2 | H | H | $COCH_3$ | $CO_2CH_3$ | $OCOCH_3$ |
| d | 3 | $COCH_3$ | H | $COCH_3$ | $CO_2CH_3$ | $OCOCH_3$ |
| e | 4 | $OCOCH_3$ | H | $COCH_3$ | $CO_2CH_3$ | $OCOCH_3$ |
| f | 5 | OH | H | H | $CO_2CH_3$ | OH |

TABLE 2-continued

Intermediates

| Compound No. | Reference Example No. | R¹ | R² | R⁶ | $X_A$ | $Y_A$ |
|---|---|---|---|---|---|---|
| g | 6 | OCOCH₃ | H | H | CO₂CH₃ | OCOCH₃ |

EXAMPLE 1

Compound a (481 mg, 1 mmol) obtained in Reference Example 1 was dissolved in 50 ml of acetic acid and 488 mg (1.1 mmol) of lead tetraacetate was added to the solution, followed by stirring under shading at room temperature for 8 hours. After the solvent was distilled off under reduced pressure, 50 ml of THF was added to the residue. The mixture was washed successively with saturated sodium bicarbonate aqueous solution and saturated sodium chloride aqueous solution and then dried over anhydrous magnesium sulfate. The solvent was distilled off under reduced pressure and the residue was purified by silica gel column chromatography (1% methanol/chloroform) to give 203 mg (40%) of Compound 1.

NMR (CDCl₃)δ: 2.08–2.44 (m, 1H), 2.20 and 2.22 (s, 3H), 3.14 and 3.18 (s, 3H), 3.42 (m, 1H), 4.04 (s, 3H), 6.36 (m, 1H), 6.64 and 6.66 (s, 1H), 7.02 (dd, 1H, J=5, 7 Hz), 7.36–7.64 (m, 5H), 7.92 (m, 1H), 8.46 (m, 1H), 9.33 (d, 1H, J=8 Hz)

MS (m/z): 512 (M+1)⁺

EXAMPLE 2

Compound b (see Table 2) [J. Antibiotics, 38, 1437 (1985)] (253 mg, 0.5 mmol) was oxidized in a similar manner as in Example 1 and subjected to silica gel column chromatography with 0.5% ethanol/chloroform as the solvent to give 191 mg (73%) of Compound 2.

NMR (CDCl₃)δ: 1.00–1.28 (m, 3H), 1.68 and 1.70 (s, 3H), 2.00–2.40 (m, 1H), 2.19 and 2.21 (s, 3H), 3.36–4.04 (m, 3H), 3.92 (s, 3H), 6.49 and 6.53 (s, 1H), 7.16–7.72 (m, 4H), 7.99 (d, 2H, J=8 Hz), 8.34 (d, 1H, J=8 Hz), 9.16 (d, 1H, J=8 Hz)

MS (m/z): 554 (M+1)⁺

EXAMPLE 3

Compound 2 (1.01 g, 1.87 mmol) obtained in Example 2 was dissolved in 50 ml of dichloromethane and 1.81 ml of 28% sodium methylate was added to the solution under ice cooling. The mixture was stirred at the same temperature for 0.5 hour. To the reaction solution was added 10 ml of saturated sodium chloride aqueous solution. After the dichloromethane layer was separated, the aqueous layer was extracted with THF and the extract was combined with the dichloromethane layer. The mixture was dried over anhydrous magnesium sulfate, and the solvent was distilled off under reduced pressure. The residue was purified by silica gel column chromatography (50% acetone/ethanol) to give 900 mg (97%) of Compound 3.

NMR (DMSO-d₆)δ: 1.16 (br, t, 3H), 1.94–2.24 (m, 1H), 2.15 (s, 3H), 3.00–4.00 (m, 3H), 3.92 (s, 3H), 6.50 (s, 1H), 7.14 (m, 1H), 7.24–8.40 (m, 7H), 9.04 (br.s, 1H), 9.13 (d, 1H, J=7 Hz)

MS (m/z): 512 (M+1)⁺

EXAMPLE 4

Compound 3 (250 mg, 0.5 mmol) obtained in Example 3 was dissolved in 10 ml of THF, and 0.74 ml of ethyl mercaptan and 10 mg of camphorsulfonic acid were added to the solution. The mixture was stirred at room temperature overnight. The solvent was distilled off under reduced pressure and the residue was purified by silica gel column chromatography (1% methanol/chloroform) to give 156 mg (59%) of Compound 4.

NMR (DMSO-d₆)δ: 1.14 and 1.16 (s, 3H), 1.90–2.88 (m, 3H), 2.13 and 2.16 (s, 3H), 3.00–3.56 (m, 1H), 3.92 (s, 3H), 6.32 (s, 0.55H), 6.45 (s, 0.45H), 6.55 and 6.57 (s, 1H), 7.00–8.00 (m, 7H), 8.32–8.56 (m, 1H), 9.12–9.26 (m, 2H)

MS (m/z): 528 (M+1)⁺

EXAMPLE 5

Compound 3 (497 mg, 1 mmol) obtained in Example 3 was dissolved in 10 ml of dioxane and 4 ml of water, and 10 mg of camphorsulfonic acid was added to the solution. The mixture was heated under reflux for 4 hours. To the reaction solution was added 20 ml of THF and the mixture was washed successively with saturated sodium bicarbonate aqueous solution and saturated sodium chloride aqueous solution and then dried over anhydrous magnesium sulfate. The solvent was distilled off under reduced pressure and the residue was purified by silica gel column chromatography (20% acetone/toluene) to give 292 mg (60%) of Compound 5.

NMR (DMSO-d₆)δ: 1.88–2.20 (m, 1H), 2.12 (s, 3H), 3.24–3.60 (m, 1H), 3.90 (s, 3H), 6.31 and 6.38 (s, 1H), 6.24 (br.s, 2H), 7.00–7.60 (m, 5H), 7.80–8.00 (m, 2H), 8.43 (m, 1H), 8.80 (s, 1H), 9.12(d, 1H, J=8 Hz)

MS (m/z): 484 (M+1)⁺

EXAMPLE 6

Compound 5 (67 mg, 0.14 mmol) obtained in Example 5 was dissolved in 2 ml of THF and 0.2 ml of water, and 16 mg (0.42 mmol) of sodium borohydride was added to the solution under ice cooling. The mixture was stirred at the same temperature for 2 hours. The reaction solution was washed with saturated sodium chloride aqueous solution and then dried over anhydrous magnesium sulfate. The solvent was distilled off under reduced pressure and the residue was triturated with THF-ether to give 53 mg (83%) of powdery Compound 6.

NMR (DMSO-$d_6$)$\delta$: 1.96–2.28 (m, 1H), 2.14 (s, 3H), 3.00–4.00 (m, 3H), 5.08 (m, 1H), 5.32–5.48 (m, 1H), 6.44 (m, 2H), 6.80–8.50 (m, 8H), 8.75 (s, 1H), 9.12 (d, 1H, J=8 Hz)

MS (m/z): 456 (M+1)+

EXAMPLE 7

Compound 4 (109 mg, 0.21 mmol) obtained in Example 4 was reduced in a similar manner as in Example 6 to give 72 mg (69%) of Compound 7.

NMR (DMSO-$d_6$)$\delta$: 1.00–1.28 (m, 3H), 1.92–2.40 (m, 1H), 2.12 and 2.16 (s, 3H), 3.00–3.40 (m, 1H), 3.80 (m, 2H), 5.08 (m, 1H), 5.36 and 5.52 (s, 1H), 6.51 and 6.53 (s, 1H), 6.96 (m, 1H), 7.12–8.52 (m, 7H), 9.14 (br, s, 1H), 9.16 (d, 1H, J=8 Hz)

MS (m/z): 500 (M+1)+

EXAMPLE 8

Compound g (227 mg, 0.41 mmol) obtained in Reference Example 6 was oxidized in a similar manner as in Example 1 to obtain Compound (I: $R^1$=OCOCH$_3$, $R^2$=H, X=CO$_2$CH$_3$, Y=COCH$_3$, Z=OCH$_3$). The obtained compound was treated in a similar manner as in Example 5 to give Compound (I: $R^1$=OCOCH$_3$, $R^2$=H, X=CO$_2$CH$_3$, Y=COCH$_3$, Z=OH). Without purifying this compound, the protective groups were removed in a similar manner as in Example 3 to give 25 mg (12.6%) of Compound 8.

NMR (CDCl$_3$-DMSO-$d_6$)$\delta$: 2.00–2.36 (m, 1H), 2.16 and 2.19 (s, 3H), 3.08–3.48 (m, 1H), 3.99 (s, 3H), 6.20–6.60 (m, 3H), 6.84–8.04 (m, 5H), 8.36–8.76 (m, 3H), 8.89 (s, 1H)

MS (m/z): 500 (M+1)+

REFERENCE EXAMPLE 1

A solution of 184 mg (0.4 mmol) of K-252 in 2 ml of DMF was ice cooled and 19.2 mg (0.4 mmol) of 50% oily sodium hydride was added to the solution. After 20 minutes, 25 μl (0.4 mmol) of methyl iodide was added to the mixture, followed by stirring for one hour. To the reaction mixture was added 20 ml of chloroform, and the resulting solution was washed with water and dried over anhydrous sodium sulfate. The solvent was removed under reduced pressure and the residue was purified by silica gel column chromatography (chloroform) to give 65 mg (34%) of Compound a as pale yellow powder.

Melting point: 250°–252° C. (recrystallized from chloroform-methanol)

NMR (CDCl$_3$)$\delta$: 9.42 (d, 1H, J=8 Hz), 8.1–7.85 (m, 2H), 7.7–7.2 (m, 5H), 7.03 (dd, 1H, J=5, 7 Hz), 5.08 (s, 2H), 4.05 (s, 3H), 3.37 (dd, 1H, J=7, 14 Hz), 3.13 (s, 3H), 2.21 (s, 3H), ca. 2.20 (dd, 1H)

MS (m/z): 481 (M)+

REFERENCE EXAMPLE 2

K-252 (2 g, 4.2 mmol) was dissolved in 10 ml of THF, and 4 ml of acetic anhydride and 2.6 g of dimethylaminopyridine were added to the solution. After being stirred at room temperature overnight, the reaction solution was washed successively with 2% hydrochloric acid aqueous solution and saturated sodium chloride aqueous solution and then dried over anhydrous magnesium sulfate. The solvent was distilled off under reduced pressure and the residue was purified by silica gel column chromatography (chloroform) to give 2.12 g (94%) of Compound c and pale yellow powder.

NMR (CDCl$_3$)$\delta$: 1.76 (s, 3H), 2.03 (dd, 1H, J=5, 14 Hz), 2.16 (s, 3H), 2.56 (s, 3H), 3.86 (dd, 1H, J=7, 14 Hz), 3.98 (s, 3H), 5.07 (s, 2H), 6.93 (dd, 1H, J=5, 7 Hz), 7.14–7.66 (m, 5H), 7.80–8.00 (m, 2H), 9.02 (d, 1H, J=8 Hz)

REFERENCE EXAMPLE 3

Compound c (110 mg, 0.2 mmol) obtained in Reference Example 2 was dissolved in 10 ml of dichloromethane, and 133 mg (1 mmol) of aluminum chloride and 0.015 ml (0.2 mmol) of acetyl chloride were added to the solution under ice cooling. The mixture was stirred at the same temperature for 2 hours. To the mixture was added 10 ml of water, and the organic layer was separated. The organic layer was then washed with saturated sodium chloride aqueous solution and dried over anhydrous magnesium sulfate. The residue was purified by silica gel column chromatography (chloroform) and recrystallized from chloroform-methanol to give 60 mg (50.8%) of Compound d as colorless prisms having an melting point higher than 300° C.

NMR (CDCl$_3$)$\delta$: 1.76 (s, 3H), 1.09 (dd, 1H, J=5, 14 Hz), 2.28 (s, 3H), 2.52 (s, 3H), 2.69 (s, 3H), 3.93 (dd, 1H, J=7, 14 Hz), 4.01 (s, 3H), 5.20 (s, 3H), 6.89 (dd, 1H, J=5, 7 Hz), 7.28–7.72 (m, 3H), 7.88–8.24 (m, 3H), 9.68 (s, 1H)

MS (m/z): 594 (M+1)+

REFERENCE EXAMPLE 4

Compound d (20 mg, 0.033 mmol) obtained in Reference Example 3 was dissolved in 1 ml of chloroform, and 25 mg (0.15 mmol) of m-chloroperbenzoic acid was added to the solution twice at an interval of one hour, followed by heating under reflux for 3 hours. After washing with saturated sodium bicarbonate aqueous solution and water, the mixture was dried over anhydrous magnesium sulfate. The solvent was distilled off under reduced pressure, and the residue was purified by silica gel column chromatography (chloroform) and recrystallized from chloroform-ether to give 10 mg (48.0%) of Compound e as brown powder having a melting point higher than 300° C.

NMR (CDCl$_3$)$\delta$: 1.79 (s, 3H), 2.09 (dd, 1H, J=5, 14 Hz), 2.26 (s, 3H), 2.40 (s, 3H), 2.70 (s, 3H), 3.94 (dd, 1H, J=7, 14 Hz), 4.00 (s, 3H), 5.34 (s, 2H), 6.98 (dd, 1H, J=5, 7 Hz), 7.20–7.70 (m, 3H), 7.92–8.20 (m, 3H), 8.90 (d, 1H, J=2 Hz)

MS (m/z): 610 (M+1)+

REFERENCE EXAMPLE 5

Compound f (0.3 g, 38.8%) was obtained from 1.0 g (1.6 mmol) of Compound e obtained in Reference Example 4 in a similar manner as in Example 3 as reddish brown prisms having melting point higher than 300° C. (recrystallized from chloroform).

NMR (DMSO-d$_6$)δ: 1.97 (dd, 1H, J=5, 14 Hz), 2.12 (s, 3H), 3.35 (dd, 1H, J=7, 14 Hz), 3.92 (s, 3H), 5.01 (s, 2H), 6.32 (s, 1H), 6.88–7.16 (m, 2H), 7.28–7.64 (m, 2H), 7.72 (d, 1H, J=8 Hz), 7.80–8.20 (m, 2H), 8.60 (s, 1H), 8.71 (d, 1H, J=2 Hz), 9.10 (s, 1H)

MS (m/z): 481 (M+1)$^+$

REFERENCE EXAMPLE 6

Compound f (241 mg, 0.5 mmol) obtained in Reference Example 5 was dissolved in 5 ml of pyridine and 1 ml of acetic anhydride was added to the solution, followed by stirring at room temperature for 6 days. The solvent was distilled off under reduced pressure and the residue was purified by silica gel column chromatography (1% methanol/chloroform) to give 247 mg (87.3%) of Compound g.

NMR (DMSO-d$_6$)δ: 1.69 (s, 3H), 2.04–2.40 (m, 1H), 2.23 (s, 3H), 2.36 (s, 3H), 3.88 (dd, 1H, J=7, 14 Hz), 3.94 (s, 3H), 5.03 (s, 2H), 7.20–8.20 (m, 6H), 8.67 (s, 1H), 8.88 (d, 1H, J=2 Hz)

MS (m/z): 568 (M+1)$^+$

EXPERIMENTAL EXAMPLE

Compound (I) obtained by the present invention was examined for C-kinase inhibitory activity and cell growth inhibitory activity by the following methods. The results are shown in Table 3.

C-Kinase inhibitory activity test:

C-Kinase inhibitory activity of representative Compounds (I) was measured in accordance with the method of Y. Nishizuka, et al. [J. Biol. Chem., 257, 13341 (1982)]. The test was carried out on test compounds at varied concentrations, and the concentration at which the enzyme activity was inhibited 50% (IC$_{50}$) was determined.

Cell growth inhibition tests:

(1) MCF7 cell growth inhibition test:

MCF7 cells (4.5×10$^4$ cells/ml) pepared in RPMI 1640 medium containing 10% fetal calf serum, 10 μg/ml insulin and 10$^{-8}$M estradiol are put into wells of a 96-well microtiter plate in the amount of 0.1 ml per each well. After incubation at 37° C. overnight in CO$_2$-incubator, 0.05 ml of a test sample appropriately diluted with the culture medium is added to each well. The cells are further cultured in CO$_2$-incubator, and then the culture supernatant is removed and the wells are washed once with PBS(−). Thereafter, 0.1 ml of fresh medium is added to each well, followed by culturing at 37° C. for 72 hours in CO$_2$-incubator. After the culture supernatant is removed, 0.1 ml of the culture medium containing 0.02% Neutral Red is added to each well, followed by culturing at 37° C. for one hour in CO$_2$-incubator, whereby the cells are stained. Then, the culture supernatant is removed and the cells are washed once with physiological saline. The pigment is extracted with 0.001N hydrochloric acid/30% ethanol and absorption is measured at 550 nm with a microplate reader. By comparing the absorption of intact cells with those of the cells treated with a test compound at known concentrations, the concentration of the test compound at which growth of the cells is inhibited 50% is calculated as IC$_{50}$.

(2) HaLaS$_3$ cell growth inhibition test:

HeLaS$_3$ cells (3×10$^4$ cells/ml) prepared in MEM medium containing 10% fetal calf serum and 2 mM glutamine are put into wells of a 96-well microtiter plate in the amount of 0.1 ml per each well.

Thereafter, the test is carried out in the same manner as in (1).

(3) COLO320DM cell growth inhibition test:

COLO320DM cells (10$^5$ cells/ml) prepared in RPMI 1640 medium containing 10% fetal calf serum, 100 U/ml penicillin and 100 μg/ml streptomycin are put into wells of a 96-well microtiter plate in the amount of 0.1 ml per each well. Thereafter, the test is carried out in the same manner as in (1) except that the cells are counted with a microcell counter. By comparing the number of intact cells with those of the cells treated with a test compound at known concentrations, the concentration of the test compound at which growth of the cells is inhibited 50% is calculated as IC$_{50}$.

TABLE 3

C—Kinase Inhibitory Activity and Cell Growth Inhibitory Activity of Synthesized Compounds

| Compound No. | IC$_{50}$ (μg/ml) | | | |
|---|---|---|---|---|
| | C—Kinase | HeLaS$_3$ | MCF7 | COLO320DM |
| 5 | 1.2 | 1.53 | 0.80 | 2.55 |
| 7 | 0.18 | 1.43 | 5.08 | 1.00 |
| K-252 (reference compound) | 0.016 | 0.2 | 0.51 | 0.27 |

What is claimed is:

1. A K-252 compound represented by the formula:

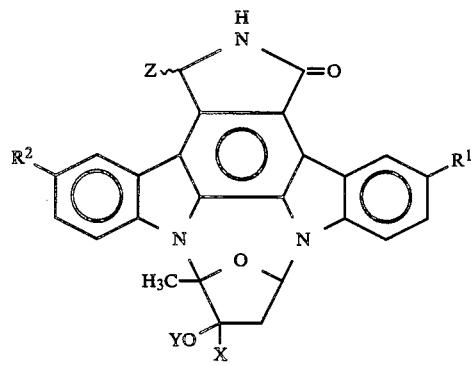

wherein R$^1$ and R$^2$ are independently H or OH; X represents COOH, COOR or CH$_2$OH; Y represents H, R or COR; and Z represents OH, OR or SR, wherein R represents lower alkyl.

2. A compound according to claim 1, wherein the lower alkyl is a straight chain or branched alkyl having 1 to 4 carbon atoms.

3. A compound according to claim 1, wherein Z is OH.

4. A compound according to claim 1, wherein Z is OR.

5. A compound according to claim 1, wherein Z is SR.

6. A compound according to claim 1, wherein R$^1$ and R$^2$ are H, X is COOCH$_3$, Y is CH$_3$ and Z is OCH$_3$.

7. A compound according to claim 1, wherein R$^1$ and R$^2$ are H, X is COOCH$_3$, Y is COCH$_3$ and Z is OC$_2$H$_5$.

8. A compound according to claim 1, wherein R$^1$ and R$^2$ are H, X is COOCH$_3$, Y is H and Z is OC$_2$H$_5$.

9. A compound according to claim 1, wherein R$^1$ and R$^2$ are H, X is COOCH$_3$, Y is H and Z is SC$_2$H$_5$.

10. A compound according to claim 1, wherein R$^1$ and R$^2$ are H, X is COOCH$_3$, Y is H and Z is OH.

11. A compound according to claim 1, wherein $R^1$ and $R^2$ are H, X is $CH_2OH$, Y is H and Z is OH.

12. A compound according to claim 1, wherein $R^1$ and $R^2$ are H, X is $CH_2OH$, Y is H and Z is $SC_2H_5$.

13. A compound according to claim 1, wherein $R^1$ is OH, $R^2$ is H, X is $COOCH_3$, Y is H and Z is OH.

14. A pharmaceutical composition comprising a pharmaceutical carrier and, as an active ingredient, an effective amount of a K-252 compound defined in claim 1.

15. A method for treating diseases due to protein kinase C which comprises administering to a human an effective amount of a pharmaceutical composition comprising a K-252 compound defined in claim 1 and a pharmaceutical carrier.

* * * * *